(12) United States Patent
Morita et al.

(10) Patent No.: US 8,574,211 B2
(45) Date of Patent: Nov. 5, 2013

(54) STRETCHABLE COMPOSITE SHEET

(75) Inventors: Shinnosuke Morita, Tochigi (JP); Kenji Ando, Tochigi (JP); Kenji Ishiguro, Tochigi (JP); Manabu Matsui, Tochigi (JP)

(73) Assignee: Kao Corporation, Tokyo (JP)

( * ) Notice: Subject to any disclaimer, the term of this patent is extended or adjusted under 35 U.S.C. 154(b) by 664 days.

(21) Appl. No.: 12/680,480

(22) PCT Filed: Dec. 1, 2008

(86) PCT No.: PCT/JP2008/071799
§ 371 (c)(1),
(2), (4) Date: Mar. 26, 2010

(87) PCT Pub. No.: WO2009/075197
PCT Pub. Date: Jun. 18, 2009

(65) Prior Publication Data
US 2010/0234823 A1    Sep. 16, 2010

(30) Foreign Application Priority Data

Dec. 10, 2007  (JP) .................................. 2007-319011
Nov. 13, 2008  (JP) .................................. 2008-291470

(51) Int. Cl.
*A61F 13/15* (2006.01)
(52) U.S. Cl.
USPC .................. 604/385.22; 604/385.24; 442/328
(58) Field of Classification Search
USPC .................. 604/385.22, 385.24; 442/328–329
See application file for complete search history.

(56) References Cited

U.S. PATENT DOCUMENTS

| 4,655,760 | A | * | 4/1987 | Morman et al. .......... 604/385.26 |
| 4,891,258 | A | * | 1/1990 | Fahrenkrug ................... 428/138 |
| 5,167,897 | A | | 12/1992 | Weber et al. |
| 5,576,090 | A | | 11/1996 | Suzuki |

(Continued)

FOREIGN PATENT DOCUMENTS

| CN | 1406568 A | 4/2003 |
| CN | 1738584 A | 2/2006 |

(Continued)

OTHER PUBLICATIONS

English translation of International Preliminary Report on Patentability (Form PCT/IB/338 and 373) and of Written Opinion of the International Searching Authority issued on Aug. 19, 2010 in PCT/JP2008/071799.

(Continued)

*Primary Examiner* — Lynne Anderson
(74) *Attorney, Agent, or Firm* — Birch, Stewart, Kolasch & Birch, LLP

(57) ABSTRACT

A stretchable composite sheet having a number of ridges in a neat and orderly arrangement is disclosed. The stretchable composite sheet is easily produced by the process of the invention. The stretchable composite sheet is a laminate of a stretch sheet 10 and a nonstretch sheet 2. The stretch sheet 10 has first zones 14 having elastic stretchability and second zones 15 having less stretchability than the first zones 14. The first zones 14 and the second zones 15 extend in the same direction and alternate with each other. The stretch sheet 10 and the nonstretch sheet 2 are bonded over substantially the entire area of their facing sides. The stretchable composite sheet has a large number of ridges 3 on the side of the nonstretch sheet.

14 Claims, 5 Drawing Sheets

(56) References Cited

U.S. PATENT DOCUMENTS

| | | | |
|---|---|---|---|
| 5,681,302 A * | 10/1997 | Melbye et al. | 604/373 |
| 5,683,787 A * | 11/1997 | Boich et al. | 428/198 |
| 6,902,793 B2 * | 6/2005 | Ukegawa et al. | 428/181 |
| 2002/0156444 A1 | 10/2002 | Otsubo | |
| 2003/0124331 A1 | 7/2003 | Morell et al. | |
| 2003/0181120 A1 | 9/2003 | Wu et al. | |
| 2004/0127865 A1 | 7/2004 | Mitsui et al. | |
| 2004/0192140 A1 | 9/2004 | Schneider et al. | |
| 2005/0148263 A1 * | 7/2005 | Zhou et al. | 442/381 |
| 2005/0170729 A1 * | 8/2005 | Stadelman et al. | 442/329 |
| 2007/0254547 A1 | 11/2007 | Ducauchuis et al. | |
| 2008/0124996 A1 | 5/2008 | Hashimoto et al. | |
| 2009/0035527 A1 | 2/2009 | Kobayashi et al. | |
| 2009/0308524 A1 | 12/2009 | Gunji et al. | |

FOREIGN PATENT DOCUMENTS

| | | | |
|---|---|---|---|
| CN | 1756659 A | | 4/2006 |
| CN | 101541526 A | | 9/2009 |
| EP | 0321980 A2 | | 6/1989 |
| EP | 0 591 647 A2 | | 4/1994 |
| EP | 1273280 A2 | | 1/2003 |
| EP | 1362567 A2 | | 11/2003 |
| JP | 5-222601 A | | 8/1993 |
| JP | 5-228177 A | | 9/1993 |
| JP | 6-505681 A | | 6/1994 |
| JP | 8-300436 A | | 11/1996 |
| JP | 2002-283479 A | | 10/2002 |
| JP | 2005-514232 A | | 5/2005 |
| JP | 2005-520722 A | | 7/2005 |
| JP | 2006-520701 A | | 9/2006 |
| JP | 2007-307898 A | | 11/2007 |
| WO | WO 95/34264 A1 | | 12/1995 |
| WO | WO 2006/115259 A1 | | 11/2006 |
| WO | WO 2006/131950 A1 | | 12/2006 |
| WO | WO 2008060204 A1 * | | 5/2008 |

OTHER PUBLICATIONS

Office Action, including a partial English translation of the Search Report, for Chinese Application No. 200880119938.8, dated Jul. 4, 2012.

Full English Machine Translation of JP-5-222601-A published Aug. 31, 1993.

Japanese Office Action for Japanese Patent Application No. 2008-291470 dated Mar. 6, 2012 with English translation.

\* cited by examiner

STRETCHABLE COMPOSITE SHEET

TECHNICAL FIELD

The present invention relates to a stretchable composite sheet.

BACKGROUND ART

Known stretch sheet materials with wrinkles or creases include those composed of a stretch sheet and a nonstretch sheet discretely bonded to each other and having wrinkles formed of the non-bonded regions of the nonstretch sheet by the retraction or contraction of the stretch sheet (see Patent Document 1 and Patent Document 2).

There has been proposed an elastic composite material composed of an elastic sheet in its relaxed state and a base sheet in its non-extended state or in a state forming no wrinkles or creases, in which the elastic sheet is bonded to the base sheet continuously in the longitudinal direction (MD) and discontinuously in the transverse direction (CD), and the base sheet has extensibility with no retractability in the CD (see Patent Document 3).

These conventional stretch sheet materials are liable to fail to have visually attractive ridges (creases) on account of irregularity of the shape of the creases or poor shape retention of the creases. In addition, production of the conventional stretch sheet materials involves discrete bonding a stretch sheet and a nonstretch sheet, which incurs the cost of equipment or a system.

| Patent Document 1 | EP0591647A2 |
| Patent Document 2 | US2002156444A1 |
| Patent Document 3 | JP 5-222601A |

DISCLOSURE OF THE INVENTION

The stretchable composite sheet of the invention is a laminate composed of a stretch sheet and a nonstretch sheet laminated with the stretch sheet and having a first direction and a second direction perpendicular to the first direction, the stretch sheet having a first zone with elastic stretchability and a second zone with less elastic stretchability than that of the first zone, the first and the second zones extending in the first direction and alternate in the second direction, the stretch sheet and the nonstretch sheet being bonded to each other on their facing sides, the stretchable composite sheet as a whole having stretchability in at least the second direction, and the stretchable composite sheet having, in a natural, relaxed state, a large number of ridges extending in the first direction on the nonstretch sheet side in a portion where the stretch sheet and the nonstretch sheet are bonded to each other over substantially the entire area.

The process for producing a stretchable composite sheet of the invention is a process for producing a stretchable composite sheet composed of a stretch sheet and a nonstretch sheet laminated with the stretch sheet, having a first direction and a second direction perpendicular to the first direction, and having in its natural, relaxed state a large number of ridges all over the area or in at least part of the nonstretch sheet side thereof, the stretch sheet having a first zone with elastic stretchability and a second zone with less elastic stretchability than that of the first zone, and the first and second zones extending in the first direction and alternate in the second direction, the process comprising bonding the stretch sheet and the nonstretch sheet to each other via an adhesive while the stretch sheet is in its stretched state such that the two sheets are bonded on their facing sides over substantially the entire area of a portion where the large number of ridges are to form.

Furthermore, the present invention provides the stretchable composite sheet which is a laminate composed of a stretch sheet and a different sheet laminated with the stretch sheet and having a first direction and a second direction perpendicular to the first direction, the stretch sheet having a first zone with elastic stretchability and a second zone with less elastic stretchability than that of the first zone, the first and the second zones extending in the first direction and alternate in the second direction, the different sheet being a stretch sheet or an extensible sheet, the stretch sheet and the different sheet being bonded to each other on their facing sides, the stretchable composite sheet as a whole having stretchability in at least the second direction, and the stretchable composite sheet having, in a natural, relaxed state, a large number of ridges extending in the first direction on the nonstretch sheet side in a portion where the stretch sheet and the different sheet are bonded to each other substantially overall.

DETAILED DESCRIPTION OF THE INVENTION

The present invention will be described based on its preferred embodiments with reference to the accompanying drawing.

Figure 1:
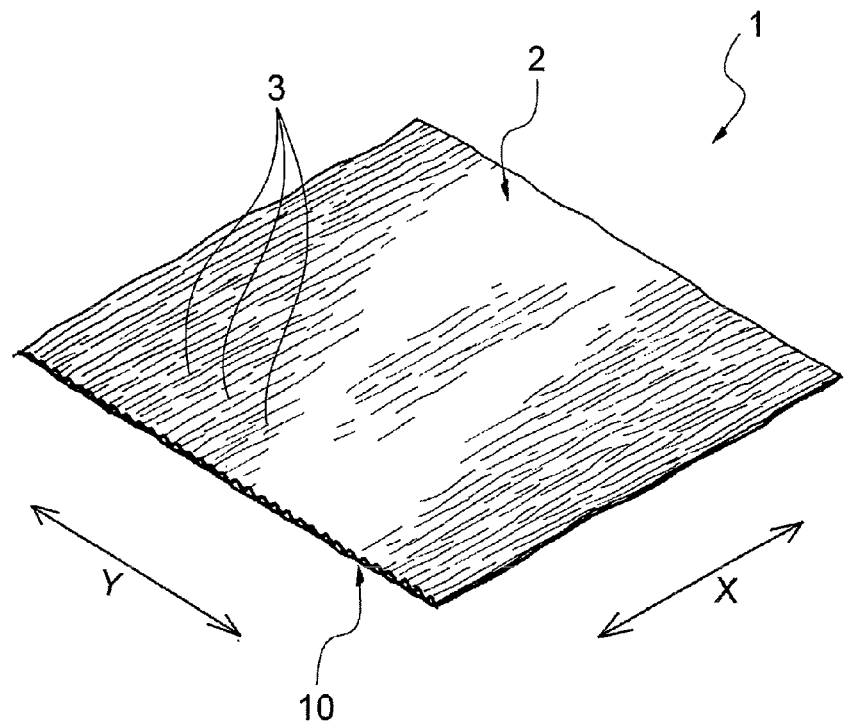
FIG. 1 is a perspective of a preferred embodiment of the stretchable composite sheet of the invention in its relaxed state.
Figure 2:
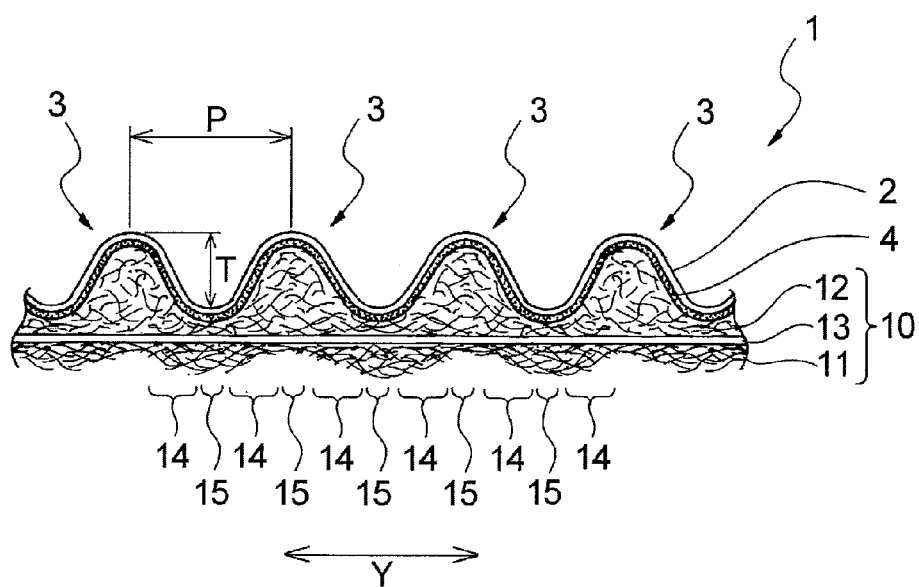
FIG. 2 is a cross-section of the stretchable composite sheet shown in FIG. 1 in its relaxed state, taken along the direction in which elastic filaments extend.

FIGS. 1 and 2 illustrate a stretchable composite sheet 1 of a preferred embodiment of the invention. The stretchable composite sheet 1 includes a stretch sheet 10 and a nonstretch sheet 2 joined to the stretch sheet 10.

Figure 3:
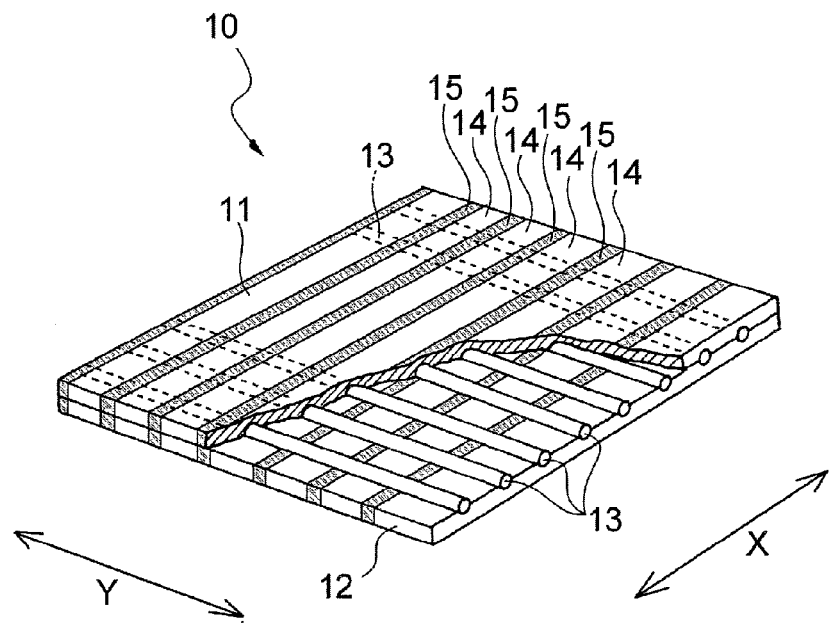
FIG. 3 is a perspective of a stretch sheet, a component of the stretchable composite sheet of FIG. 1, in its stretched state with part cut away.

As illustrated in FIG. 3, the stretch sheet 10 has first zones 14 having elastic stretchability and second zones 15 having less elastic stretchability than the first zones 14. The first and second zones 14 and 15 extend in direction X indicated in FIG. 3.

The first and second zones 14 and 15 alternate in direction Y indicated in FIG. 3. Direction X in the drawing is one of the directions parallel to the two sides of the stretchable composite sheet in which the first and second zones 14 and 15 of the stretch sheet 1 extend, and direction Y is a direction perpendicular to direction X.

The stretch sheet 10 has recoverable stretch in direction Y owing to the elastic stretchability of every first zone 14. The second zones 15 of the stretch sheet 10 have little stretch.

The nonstretch sheet 2 has substantially no stretchability. The stretchability as herein referred to means stretchability of the sheet per se.

It is desirable that the nonstretch sheet 2 has no stretchability in at least direction Y perpendicular to the direction in which the first and second zones extend (e.g., direction X), more preferably in both directions X and Y.

The nonstretch sheet 2 used in the present embodiment has substantially no stretchability in either direction X or direction Y. The nonstretch sheet 2 may have no stretchability in any direction parallel to the two sides thereof.

By the expression "a sheet has substantially no stretchability in a certain direction" is meant that the sheet shows little stretch when subjected to a pulling force in that direction. When, for example, a sample measuring 15 cm (length) by 5 cm (width) has an elongation at break of 10% or less in longitudinal pulling on a tensile tester, such as a Tensilon tester, the sample is regarded as having substantially no stretchability in the longitudinal direction.

The elongation at break as referred to herein is calculated from (length of sample at break−initial length of sample)/(initial length of sample)×100. The longitudinal direction of the sample is the above-mentioned "certain direction".

As shown in FIG. 2, the stretch sheet 10 and the nonstretch sheet 2 are bonded to each other over substantially the entire area of their facing sides via an adhesive 4 (e.g., a hot melt adhesive). As used herein, the term "over substantially the entire area" is intended to include not only the case in which the stretch sheet 10 and the nonstretch sheet 2 are bonded to each other via an adhesive applied all over the surface of one or both of them by means of, e.g., a coater gun but also the case in which the adhesive is applied between the first zones 14 and the nonstretch sheet 2 and between the second zones 15 and the nonstretch sheet 2 in a uniformly and densely distributed pattern by means of, e.g., a spray gun, a spiral gun, or a roll coater.

Bonding the stretch sheet 10 and the nonstretch sheet 2 with the adhesive 4 does not need to be done all over the area where the two sheets face to each other. It is only necessary that the two sheets are bonded together in a portion where to form ridges. The two sheets may be bonded partly or non-bonded where ridges are not to be formed. The two sheets are bonded all over the area which is designed to form ridges.

As illustrated in FIGS. 1 and 2, the stretchable composite sheet 1 of the present embodiment is in a contracted state with no outer force applied, i.e., in a natural, relaxed state. In at least the contracted state, the stretchable composite sheet 1 has a large number of ridges 3 extending in direction X on the side of the nonstretch sheet 2. The ridges 3 extend substantially parallel to the direction in which the first and second zones 14 and 15 extend, namely direction X. In the present embodiment, the first and second zones 14 and 15 are spaced at the respective constant distances in direction Y so that all the ridges 3 are almost equal in height and width.

The stretchable composite sheet 1 of the present embodiment is stretchable in direction Y until the nonstretch sheet 2 becomes practically flat, in which state the ridges 3 are flattened out. On release from the stretch, the stretchable composite sheet 1 retracts, and the ridges form again. It is only necessary that the large number of ridges 3 form at least when the stretchable composite sheet of the present embodiment is in its relaxed state.

The pitch P (see FIG. 2) of the tops of the ridges 3 and the height T (see FIG. 2) of the ridges 3 are not particularly limited and may be decided as appropriate to the intended use of the stretchable composite sheet 1. When the stretchable composite sheet 1 is used as a component of, for example, an absorbent article (e.g., as a topsheet defining the side for fluid absorption or an exterior cover of a pull-on type absorbent article, like a disposable pull-on diaper), the pitch P is preferably 0.5 to 5 mm, more preferably 1 to 3 mm, and the height T is preferably 0.5 to 5 mm, more preferably 1 to 3 mm. In the present embodiment, the pitch P of the tops of the ridges 3 is about double the pitch of the first zones 14 or the second zones 15.

Method of Measuring Pitch P and Height T:

The pitch P and the height T are measured without any outer force applied to the stretchable composite sheet 1, i.e., with the stretchable composite sheet 1 being in the contracted or relaxed state. The distance between the tops of adjacent ridges 3 and the distance between a valley formed between adjacent ridges 3 and the top of either ridge are measured in that state to give the pitch P and the height T, respectively. The measurement is taken with a laser displacement meter or by observing a cross-section of the sheet under a microscope or on a micrograph.

In order that ridges 3 form in a neat and orderly arrangement in practically parallel relation to the direction in which the first and second zones 14 and 15 extend, namely, direction X, it is desirable that, when the stretch sheet 10 is stretched in the direction perpendicular to direction X (i.e., direction Y), the stretch sheet 10 is not likely to contract in the direction perpendicular to the stretch direction (i.e., direction X), that is, is not likely to undergo contraction in width.

When the stretch sheet 10 is stretched, for example, 2.0 times the original length in the direction (direction Y) perpendicular to the direction (direction X) in which the first and second zones 14 and 15 extend, the contraction in width (in direction X) of the stretch sheet 10 is preferably such that the width retention is 70% to 100%, more preferably 80% to 100%, even more preferably 90% to 100%. The width retention (%) representing the degree of contraction in width is a percentage obtained by dividing the width after stretch with the width before stretch ((width after stretch/width before stretch)×100). In carrying out the measurement, a sample measuring 200 mm in direction Y and 100 mm in direction X is stretched 2.0 times in direction Y with the width (the dimension in direction X) of both longitudinal ends of the sample fixed at 100 mm. The width is measured at the middle of the stretched sample.

The present embodiment employs the stretch sheet 10 illustrated in FIG. 3 as a stretch sheet that is less likely to contract in width.

The stretch sheet 10 of FIG. 3 has a large number of elastic filaments 13 arranged to extend in one direction (direction Y in FIG. 3) without intersecting with each other and bonded to extensible fabric layers 11 and 12 over their whole length in their substantially nonstretched state.

Each elastic filament 13 of the stretch sheet 10 is substantially continuous over the whole length of the stretch sheet 10. The elastic filament 13 contains an elastic resin. The stretch sheet 10 has the elastic filaments 13 arranged to extend in one direction without intersecting. The stretch sheet having such a structure is characterized by less likelihood of contracting in width when stretched in the direction (direction Y) perpendicular to the direction (direction X) in which the first and second zones 14 and 15 extend as compared with a stretch sheet having elastic fibers entangled with each other. It is acceptable that the elastic filaments 13 unintentionally intersect with each other due to unavoidable fluctuation of conditions in the production of the stretch sheet 10. The individual elastic filaments 13 may extend straight or in serpentine fashion as long as they do not intersect with each other.

The elastic filaments 13 are fixed to the nonwoven fabric layers 11 and 12 in their substantially nonstretched state. The elastic filaments 13 can be synthetic or natural rubber threads or wet-spun or dry-spun (melt spun) threads. The elastic filaments 13 are preferably those as obtained by melt spinning without being wound up. The elastic filaments 13 are preferably those obtained by drawing undrawn filaments.

The elastic filaments 13 are preferably those formed by drawing a filamentous elastic resin in a molten or softened state. Drawing an elastic resin in a molten or softened state makes it possible to fix the elastic filaments 13 to the nonwoven fabric layers 11 and 12 in their unstretched state. Drawing operation can be carried out in the present embodiment by, for example, (a) a resin providing elastic filaments 13 is melt spun into undrawn filaments, and the undrawn filaments are then re-heated to or above the softening point (glass transition point Tg of the hard segments), at which they are drawn or (b) a resin providing elastic filaments 13 is melt spun, and the resulting molten resin streams are directly subjected to drawing. When the stretch sheet 10 is produced by the preferred process described infra, the elastic filaments 13 are obtained by drawing molten resin filaments directly from the melt spinning nozzles.

The elastic filament 13 as obtained by drawing preferably has a diameter of 10 to 200 μm, more preferably 20 to 130 μm. The elastic filament 13 may have a circular cross-section or can have an elliptic cross-section. With the elastic filaments 13 having the above recited diameter, they are preferably arranged at a pitch of 0.1 to 5 mm, more preferably 0.4 to 1 mm.

The elastic filament 13 is bonded to the nonwoven fabric layers 11 and 12 over the whole length thereof. As used herein, the expression "over the whole length" is not intended to mean that all the fibers in contact with an elastic filament 13, of the fibers constituting the nonwoven fabric layers 11 and 12, should be bonded to the elastic filament 13 but is intended to mean that the elastic filament 13 is bonded to the constituent fibers of the nonwoven fabric layers 11 and 12 without intentionally leaving part of them unbonded. Bonding the elastic filament to the nonwoven fabric layers 11 and 12 over its whole length achieves sufficiently ensured adhesion between the elastic filament 12 and each of the nonwoven fabric layers 11 and 12.

Modes of bonding the elastic filament 13 and the first and second nonwoven fabric layers 11 and 12 include fusion bonding and bonding using an adhesive. In a preferred mode, the elastic filaments 13 as obtained by melt spinning are fusion bonded to the nonwoven fabric before they solidify. In this mode, an adhesive may be applied as an auxiliary bonding means before the nonwoven fabric layers 11 and 12 and the elastic filaments are bonded. After the nonwoven fabric layers 11 and 12 and the elastic filaments are bonded, the resulting laminate may be subjected to heat treatment (e.g., steam jet treatment or heat embossing) or mechanical entanglement (e.g., needle punching or hydroentanglement) as an auxiliary bonding means.

The stretch sheet 10 has recoverable stretch in the same direction as the direction in which the elastic filaments 13 extend. The recoverable stretch of the stretch sheet 10 is due to the elasticity of the elastic filaments 13. When the stretch sheet 10 is pulled in the same direction as the extending direction of the elastic filaments 13, the elastic filaments and the first and second nonwoven fabric layers 11 and 12 stretch. On release from pulling, the elastic filaments 13 retract, whereby the first and second nonwoven fabric layers 11 and 12 return to the state before the pulling.

Figure 4:
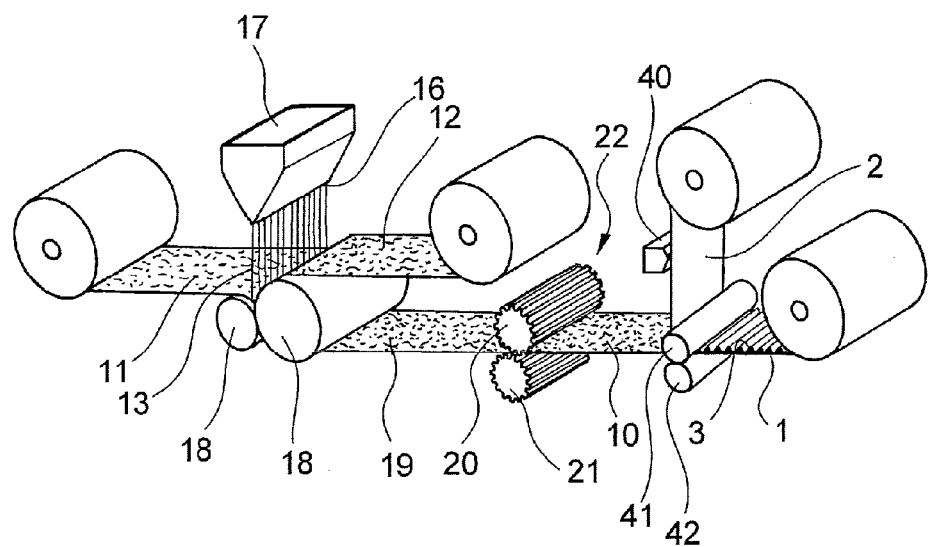
FIG. 4 is a schematic view of apparatus that is suitably used to produce the stretchable composite sheet of FIG. 1.

The stretch sheet 10 is obtained, for example, as illustrated in FIG. 4. That is, a large number of molten elastic filaments 13 extruded from a spinning nozzle 16 are fusion bonded to nonwoven fabric layers 11 and 12 before solidifying while being drawn by taking up at a predetermined speed as oriented in one direction in a non-intersection relation to each other. The laminate of the nonwoven fabric layers 11 and 12 with the elastic filaments 13 fusion bonded therebetween (i.e., a precursor of a stretch sheet 10) is then stretched in the extending direction of the elastic filaments 13 to impart extensibility to the nonwoven fabric layers 11 and 12.

FIG. 4 illustrates an embodiment of a preferred process for producing the stretchable composite sheet 1, in which the stretch sheet 10 of FIG. 3 is made and further processed to produce the stretchable composite sheet 1 in a continuous manner.

The spinning nozzle 16 is fitted to a spinning head 17. The spinning head 17 is connected to an extruder. A resin may be supplied to the spinning head 17 via a gear pump. An elastic resin is melt kneaded in the extruder and fed to the spinning head 17. A large number of the spinning nozzles 16 are fitted into the spinning head 17 in a straight linear arrangement along the transverse direction of webs of the first and second nonwoven fabric layers 11 and 12. The spacing between adjacent spinning nozzles 16 corresponds to the spacing between adjacent elastic filaments 13 in the stretch sheet 10. The orifice of each spinning nozzle 16 is usually circular. The diameter of the orifice influences the diameter and draw ratio of the elastic filament 13. From this viewpoint, the spinning nozzle 16 preferably has an orifice diameter of 0.1 to 2 mm, more preferably 0.2 to 0.6 mm. For the purpose of enhancing the adhesive strength to the nonwoven fabric layers 11 and 12, improving the spinnability into the elastic filaments 13, and improving the stretch characteristics of the stretch sheet 10, the elastic filaments 13 may be conjugate filaments having, e.g., a side-by-side configuration, a sheath/core configuration, or a sea/island configuration. The conjugate filament is preferably composed of a polypropylene elastomeric resin and a styrene elastomeric resin.

The spun, molten elastic filaments 13 are sandwiched between a web of a first nonwoven fabric layer 11 and a web of a second nonwoven fabric layer 12 that are unrolled and fed at equal speeds. The elastic filaments 13 as sandwiched are taken off at a predetermined speed, which is equal to the feed speed of the two webs. The take-off speed of the elastic filaments 13 influences the diameter and draw ratio of the elastic filaments 13. The tension of the elastic filaments 13 caused by the drawing prevents the elastic filaments 13 from being disturbed by the wind or static electricity generating in joining the elastic filaments 13 to the webs of the nonwoven fabric layers 11 and 12, whereby the elastic filaments are successfully disposed to extend in one direction without intersecting. From this point of view, it is preferred that the take-off speed of the elastic filaments 13 is controlled with respect to the resin extrusion speed through the spinning nozzle orifices so as to result in a draw ratio of 1.1 to 400, more preferably 4 to 100 times, even more preferably 10 to 80.

The elastic filaments 13 are joined to the first and second nonwoven fabric layers 11 and 12 before they solidify, that is, while they are in a fusion-bondable state. Therefore, the elastic filaments 13 are fusion bonded to the first and second nonwoven fabric layers 11 and 12 as sandwiched therebetween. To put it another way, since the elastic filaments are fusion bonded to the running webs of the nonwoven fabric layers 11 and 12 before they solidify, they are drawn while being taken off. Any external heat is applied to the first and second nonwoven fabric layers 11 and 12 in achieving the fusion bonding of the elastic filaments 13. The fusion bonding of the elastic filaments 13 to the nonwoven fabric layers 11 and 12 completes only by the heat of fusion of the fusion bondable elastic filaments 13. As a result, only the fibers present around each elastic filament 13 of the fibers constituting the nonwoven fabric layers 11 and 12 are fusion bonded to the elastic filament 13, whereas more remote fibers are not fusion bonded. Thus, the heat applied to the nonwoven fabric layers 11 and 12 is minimized, whereby the good hand essentially possessed by the nonwoven fabric itself is retained to provide the resulting stretch sheet 10 with good hand.

Until the spun elastic filaments 13 are joined with the webs of the first and second nonwoven fabric layers 11 and 12, the elastic filaments 13 are drawn to have their molecules oriented along the drawing direction and their diameter reduced. The molecular orientation provides elastic filaments 13 having a small extension/retraction hysteresis of strength at 50% elongation. In order to sufficiently draw the elastic filaments 13 and to prevent breakage of the filaments during the drawing operation, air at a prescribed temperature (hot air or cold air) may be blown to the spun elastic filaments 13 to control the temperature of the filaments 13.

The elastic filament 13 may be drawn not only in its molten state (melt drawing) but in a softened state in the course of cooling. The term "molten state" means a state of a resin that flows when subjected to an outer force. The melting point of a resin is measured as a peak of tan δ obtained by viscoelasticity measurement (for example, an oscillatory strain is applied to a resin between parallel disks in the rotation direction). It is recommended to provide a sufficiently long drawing zone so as to avoid breakage of the filaments being drawn. From the same viewpoint, the elastic resin preferably has a melting temperature of 130° C. to 300° C. In terms of heat resistance (resistance to molding temperature) of the elastic resin, the melting temperature preferably ranges 130° C. to 220° C. The softening point is obtained as a Tg, one of the viscoelastic characteristics of the elastic resin as measured on a sheet-shaped specimen. By the term "softened state" is meant a state between the softening point and the melting point. The elastic resin preferably has a softening point of 60° C. or higher, more preferably 80° C. to 180° C., in view of elastic resin crystal growth during storage of the stretch sheet 10 and reduction in stretch characteristics of the stretch sheet 10 by a body temperature.

It is preferred for the elastic filaments being joined to the webs of the nonwoven fabric layers 11 and 12 to have a temperature of 100° C. or higher so as to ensure fusion bonding to the fibers. It is preferred for the elastic filaments to have a temperature of 180° C. or lower, more preferably 120° C. to 160° C., thereby to retain their shape and to provide a stretch sheet 10 with good stretch characteristics. The temperature of the filament being bonded (hereinafter referred to as a bonding temperature) is measurable by using, as a laminating material, film (e.g., of modified polyethylene or modified polypropylene) having a melting point different from that the elastic resin of the elastic filament and observing the bonding condition between the filament and the film. When the elastic filament and the film are fusion bonded to each other, then the bonding temperature is at or above the melting point of the laminating film.

The elastic filament 13 is in a substantially nonstretched state (incapable of contraction when released from outer force) at the time of bonding to the nonwoven fabric layers 11 and 12. In order to obtain sufficient tenacity of the bond, it is preferred that, when the elastic filament 13 and the nonwoven fabric layers 11 and 12 are joined to each other, at least part of the fibers constituting the nonwoven fabric layers 11 and 12 is fused and bonded to the elastic filament. It is more preferred that both the elastic filament 13 and at least part of the fibers constituting the nonwoven fabric layers 11 and 12 are fused and bonded to each other. The stretch characteristics of the resulting stretch sheet 10 are influenced by the density of the bonds between the elastic filaments 13 and the nonwoven fabric layers 11 and 12. The stretch characteristics are controllable by the bonding temperature, bonding pressure, and debonding of the bonds by the stretch (described infra) of the nonwoven fabric layers 11 and 12. Fusion bonding the constituent fibers of the nonwoven fabric layers 11 and 12 to the elastic filaments 13 increases the strength of the individual bonds. It is advantageous to lower the bond density in that stretch hindrance by the nonwoven fabric layers 11 and 12 is lessened and that the resulting stretch sheet 10 has sufficient bond strength.

The elastic filaments 13 are joined to the first and second nonwoven fabric layers 11 and 12 as arranged to extend in one direction in a non-intersection relation to each other. The nonwoven fabric layers 11 and 12 thus having the elastic filaments 13 sandwiched therebetween are then passed between a pair of nip rollers 18. The pressing conditions affect the hand of the resulting stretch sheet 10. Too high a nip pressure tends to cause the elastic filaments 13 to bite into the nonwoven fabric layers 11 and 12, which can result in poor hand of the stretch sheet 10. In view of this, an excessively high nip pressure is not needed. Such a nip pressure that brings the elastic filaments 13 into contact with the nonwoven fabric layers 11 and 12 would be enough.

Also included in the pressing conditions of the nip rollers 18 is the temperature of the nip rollers 18. The inventors' study has revealed that a stretch sheet 10 with a better hand is obtained when the nip rollers 18 are not heated (that is, left to nature) or are positively cooled rather than when the nip rollers 18 are heated. Where the nip rollers 18 are cooled, the surface temperature of the nip rollers 18 is preferably set between 10° C. and 15° C. using a coolant, such as cooling water.

There is thus obtained a composite web 19 having two webs of nonwoven fabric layers 11 and 12 and the elastic filaments 13 interposed therebetween. In the composite web 19 the webs of the nonwoven fabric layers 11 and 12 are essentially inextensible. The composite web 19 as obtained is a precursor of the stretch sheet 10.

The composite web 19 including the webs of nonwoven fabric layers 11 and 12 is stretched in the extending direction of the elastic filaments 13 to form first zones 14 having elastic stretchability and second zones 15 having less elastic stretchability than the first zones 14.

As shown in FIG. 4, the stretch processing is carried out in the present embodiment by the use of a stretching unit 22 having an intermeshing pair of toothed rollers 20 and 21 each having alternating teeth (ridges) and bottoms (grooves) in the peripheral direction thereof. That is, the composite web 19 is stretched in the machine direction, i.e., the extending direction of the elastic filaments 13 while being passed between a pair of the toothed rollers 20 and 21.

The stretching unit 22 has a known vertical displacement mechanism (not shown) for vertically displacing the shaft of either one of or both of the toothed rollers 20 and 21 to adjust the clearance between the rollers 20 and 21. In the present embodiment, the toothed rollers 20 and 21 are configured such that the teeth of the toothed roller 20 fit with clearance into the spaces between every adjacent teeth of the other toothed roller 21 and that the teeth of the other toothed roller 21 fit with clearance into the spaces between every adjacent teeth of the toothed roller 20. The composite web 19 is introduced into the nip between the so configured toothed rollers 20 and 21 to be stretched.

Each of the toothed rollers 20 and 21 may be a drive roller attached to a motor, or either one of them may be a drive roller (and the other is a driven roller). In this particular embodiment, only the lower toothed roller 21 is attached to a motor, while the upper toothed roller 20 is not attached to a motor and is driven by the intermeshing drive roller 21. To use a driven roller is advantageous in that the composite web 19 is stretched to form first zones 14 and second zones 15 in clear stripes. The toothed rollers 20 and 21 may have a common involute or cycloid tooth profile. An involute or cycloid tooth profile with a reduced tooth thickness is particularly preferred.

Figure 5:
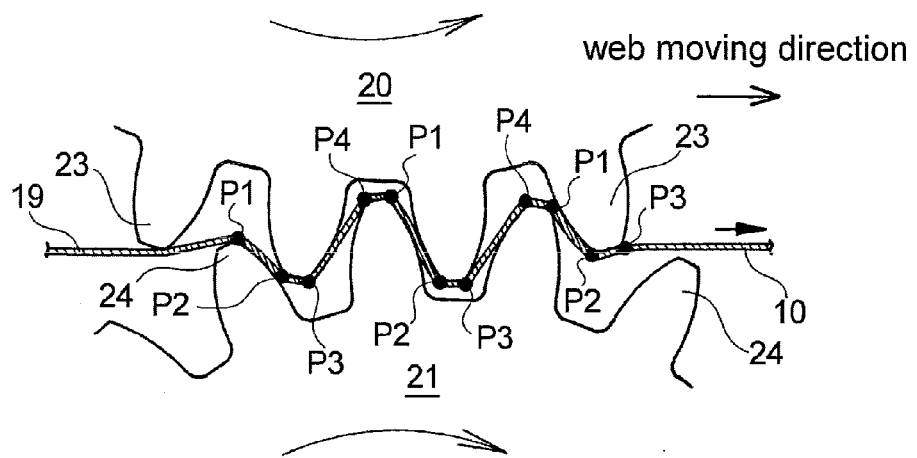
FIG. 5 schematically illustrates a stretch sheet precursor being stretched in the apparatus of FIG. 4.

FIG. 5 schematically illustrates the composite web 19 being stretched. While the composite web 19 is passed between the toothed rollers 20 and 21, the regions of the composite web 19 that come into contact with the top lands of the teeth 23 and 24 of the toothed rollers 20 and 21, respectively (i.e., the regions between P3 and P2 and regions between P1 and P4, respectively), are little stretched. On the other hand, the regions of the composite web 19 that are pressed by the tooth surface of the teeth 24 of the drive toothed roller 21 onto the tooth surface of the teeth 23 of the driven toothed roller 20 (e.g., the regions between P2 and P1) are largely stretched by the toothed rollers 20 and 21. The regions of the composite web 19 that are separated away from the teeth 23 of the toothed roller 20 by the tips of the teeth 24 of the toothed roller 21 (i.e., the regions between P4 and P3) are also stretched largely while not so largely as the regions between P2 and P1.

Although the regions in contact with the top lands of the teeth 23 and 24 of the toothed rollers 20 and 21 (the regions between P3 and P2 and the regions between P1 and P4) are little stretched as stated, they become thinner because they are pressed radially, i.e., in the thickness direction from one side. The regions between P3 and P2 and the regions between P1 and P4 are opposite in direction of thickness reduction because the directions of pressing are opposite to each other.

As a result of the above-described stretch processing, the webs of the nonwoven fabric layers 11 and 12 in the regions of the composite web 19 that are largely stretched (the regions between P2 and P1 and the regions between P4 and P3) undergo physical changes that allow them to extend, such as extension of the constituent fibers per se, debonding of the bonds between the fibers, deformation of the three-dimensional structure formed of a plurality of the fibers, and breakage of the constituent fibers. On the other hand, such changes do not occur in the nonwoven fabric layers 11 and 12 in regions that are little stretched (the regions between P3 and P2 and the regions between P1 and P4).

The regions that are largely stretched (the regions between P2 and P1 and the regions between P4 and P3) become the first zones 14 having elastic stretchability, and the regions that are stretched little (the regions between P3 and P2 and the regions between P1 and P4) become the second zones 15 having less stretchability than the first zones 14.

Thus, the stretch processing processes the composite web 19 into a stretch sheet 10 having the first and second zones 14 and 15 in an alternating configuration.

The stretching unit 22 is not limited to the type composed of rollers as used in the present embodiment. Other usable stretching units include one composed of a pair of conveyor belts each having a large number of continuous ridges extending in the direction perpendicular to the machine direction.

Still other usable stretching units include one composed of a pair of uneven plates each having on their facing side a large number of ridges in the direction perpendicular to the machine direction, and a displacement mechanism for displacing the plates from an isolated position to a biting position by using cam mechanism to widen and shorten the distance between both the plates.

In the process of the present embodiment, the stretch sheet 10 is transferred in its stretched state and joined and bonded to a nonstretch sheet 2 in the stretched state as illustrated in FIG. 4. The term "stretched state" as used herein does not mean the state of the composite web 19 stretched by the engagement of the toothed rollers 20 and 21 but that the stretch sheet 10 having the alternating first and second zones 14 and 15 is stretched from its relaxed (contracted) state.

It is preferred that the stretch sheet 10 to be bonded to the nonstretch sheet 2 is in a 1.1 to 4.0 times stretched state, more preferably a 1.2 to 3.0 times stretched state, even more preferably 1.5 to 2.5 times stretched state, in the machine direction to provide a stretchable composite sheet having easy stretch and easy retraction. The stretch ratio of the stretch sheet 10 is obtained by dividing the length after stretch by the natural (relaxed) length before stretch.

The amount of an adhesive applied as represented by coating weight is preferably at least 0.2 $g/m^2$, more preferably 0.5 to 20 $g/m^2$, even more preferably 0.5 to 10 $g/m^2$, still more preferably 0.5 to 5 $g/m^2$, to secure adhesive strength and not to hinder the stretch and retraction of the resulting stretchable composite sheet.

In the present embodiment, an adhesive (preferably a hot melt adhesive) is applied to the nonstretch sheet 2 immediately before joined to the stretch sheet 10 by means of an adhesive applicator 40. The adhesive may be applied to the stretch sheet 10 or both the stretch sheet 10 and the nonstretch sheet 2. In any case, the amount of the adhesive applied as recited above is a total weight of the adhesive applied to the stretch sheet 10 and the nonstretch sheet 2 per square meter of the stretchable composite sheet in its natural, relaxed state.

In the present embodiment, the adhesive is continuously applied in the moving direction of the nonstretch sheet 2 over the entire area of a portion to be joined to the stretch sheet 10 of the nonstretch sheet 2. Therefore, there is produced no difference on the nonstretched sheet in amount of the adhesive applied and application pattern between the regions to be joined to the first zones 14 and the regions to be joined to the second zones 15.

The stretch sheet 10 and the nonstretch sheet 2 are introduced into the nip of a pair of nip rollers 41 and 42 simultaneously with or immediately after their joining, whereby the two sheets are united into a stretchable composite sheet 1.

Figure 6:
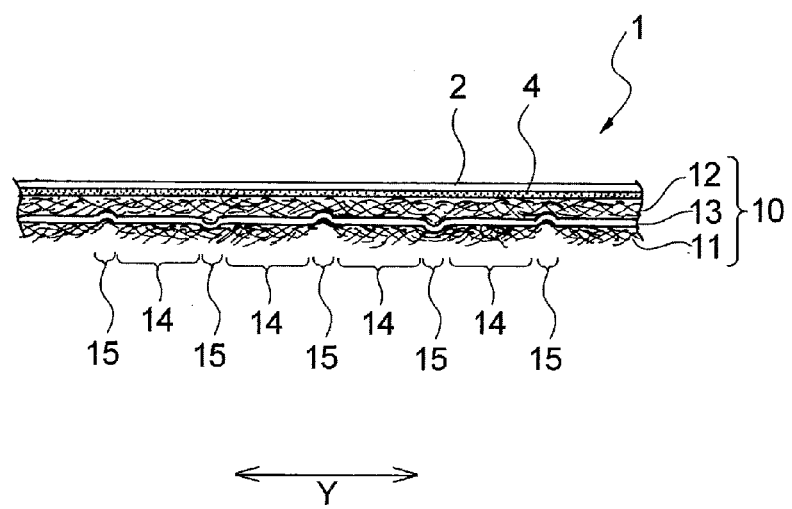
FIG. 6 is a cross-section of the stretchable composite sheet of FIG. 1 in its stretched state, taken along the direction in which elastic filaments extend.

When the resulting stretchable composite sheet 1 is under tension to be in the same stretched state as of the stretch sheet 10 being bonded to the nonstretch sheet 2, it takes on a flat shape with no ridges 3 as illustrated in FIG. 6. On reducing or removing the tension, the stretchable composite sheet 1 retracts to form ridges 3 as illustrated in FIG. 2. In FIG. 6, the second zones 15 formed by the contact with the top lands of the teeth of one of the toothed rollers and those formed by the contact with the top lands of the teeth of the other toothed roller are depicted as having oppositely directed curves to make them easily distinguishable just for the sake of convenience.

According to the process of producing the stretchable composite sheet 1 illustrated in FIG. 4, the stretchable composite sheet 1 is relaxed from tension immediately after joining the stretch sheet 10 and the nonstretch sheet 2 and taken up as relaxed in a roll form. The stretchability of the stretchable composite sheet 1 and the shape of the ridges 3 are maintained stably by storing the sheet in a non- or low-stretched state.

Figure 7:
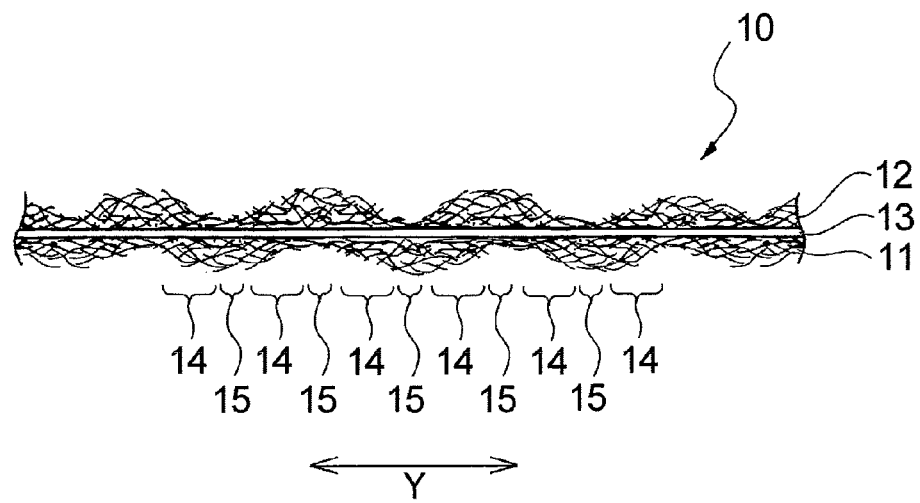
FIG. 7 is a cross-section of the stretch sheet of FIG. 3 in its contracted (relaxed) state, taken along the direction in which elastic filaments extend.

When the stretch sheet 10 in a stretched state before being joined to the nonstretch sheet 2 is retracted, the stretch sheet 10 takes on the shape illustrated in FIG. 7, in which the stretch sheet 10 regularly forms mild ridges continuously at a constant pitch in direction Y in correspondence with the pitches of the first and second zones 14 and 15 on both sides thereof. In a region where a second region 15 forms a protrusion on one side thereof, a depression forms on the other side (the opposite side) of that region. Conversely, in a region where a second region 15 forms a depression on one side thereof, a protrusion forms on the other side. Thus, the protrusions on one side and those on the other side alternate with each other.

When the stretch sheet 10 is retracted from the state shown in FIG. 6, the nonstretch sheet 2 does not contract per se but absorbs the retraction by deformation. As a result, ridges 3 form regularly in the stretchable composite sheet 1 in correspondence with the pitches of the first and second zones 14 and 15.

Since the stretch sheet 10 and the nonstretch sheet 2 are bonded all over, the ridges 3 contain the fibers of the nonwoven fabric layer 12 as shown in FIG. 2. The stretchable composite sheet 1 therefore has excellent cushioning and elastic properties. The stretchable composite sheet 1 provides a good feel to the touch when used as, for example, a topsheet, which comes into direct contact with the skin, of an absorbent article, such as a sanitary napkin or a diaper.

Since the stretch sheet 10 and the nonstretch sheet 2 are bonded with an adhesive, the stretchable composite sheet 1 is softer and more pleasing to the touch than when bonded by heat sealing, embossing, and the like.

With the nonstretch sheet 2 fully stretched (see FIG. 6), the stretchable composite sheet 1 no longer stretches. Therefore, when the stretchable composite sheet 1 is used in a continuous line of manufacturing, for example, an absorbent article such as a sanitary napkin or a diaper, excessive stretch of an assembly or a subassembly in the machine direction (direction Y of the stretchable composite sheet 1) is prevented. This provides very stable conveyance of the assembly or the subassembly, facilitating high speed manufacturing and accurate processing.

Furthermore, the stretchable composite sheet 1, when used as a component of an absorbent article such as a sanitary napkin or a diaper, provides good fit and high breathability, i.e., air permeability owing to the ridges.

Materials of the first and second nonwoven fabric layers 11 and 12 and the elastic filaments 13 that compose the stretch sheet 10 will be described. The fibers that can be used to make the nonwoven fabric layers 11 and 12 include fibers of polyethylene (PE), polypropylene (PP), polyesters (PET and PBT), and polyamides. The fibers composing the nonwoven fabric layers 11 and 12 may be staple fibers or continuous fibers and hydrophilic or water repellent. Sheath/core or side-by-side conjugate fibers, split fibers, modified cross-section fibers, crimped fibers, and heat shrunken fibers are also useful. These fibers may be used either individually or in combination of two or more thereof. The nonwoven fabric layers 11 and 12 may be nonwoven fabrics of continuous filaments or staple fibers. The nonwoven fabric layers 11 and 12 are preferably formed of staple fiber nonwoven fabric to provide a thick and bulky stretch sheet 10. In the case where the side of the stretch sheet 10 is adapted to be brought into contact with the skin of a wearer, staple fiber nonwoven fabric with good hand may be used on the side adapted to be brought into contact with the skin, whilst continuous filament nonwoven fabric with high strength may be used on the opposite side.

It is preferred that the fibers composing each nonwoven fabric layer 11 or 12 are made up of at least two components including a low melting component and a high melting component. At least the low melting component is fused to bond the fibers at their intersections. Preferred examples of a sheath/core conjugate fiber made up of at least two components including a low melting component and a high melting component are those having a high melting PET or PP as a core and a low melting PET, PP or PE as a sheath. The use of such conjugate fibers is particularly preferred to enhance the fusion bonding to the elastic filaments 13 and reduce likelihood of debonding from the elastic filaments 13.

The elastic filament 13 is made, e.g., from thermoplastic elastomers or rubbers. Use of elastic filaments made from a thermoplastic elastomer is preferred to make the stretch sheet used in the present embodiment. This is because, for one thing, a thermoplastic elastomer is melt-spinnable using an extruder in the same manner as ordinary thermoplastic resins. For another, the filaments thus obtained are easy to fusion bond. Examples of the thermoplastic elastomers include styrene elastomers, such as SBS (styrene-butadiene-styrene), SIS (styrene-isoprene-styrene), SEBS (styrene-ethylene-butylene-styrene), and SEPS (styrene-ethylene-propylene-styrene); olefin elastomers, such as an ethylene-based copolymer with an α-olefin and a propylene-based copolymer with ethylene, butene, and octene or the like; polyester elastomers; and polyurethane elastomers. These elastomers may be used either individually or in combination of two or more thereof. Sheath/core or side-by-side conjugate fibers composed of these resins are also useful. Elastic filaments made from a styrene elastomer, an olefin elastomer or a combination thereof are particularly preferred in view of spinnability, stretch characteristics, and cost for the elastic filaments 13.

A preferred combination of materials of the elastic filaments 13 and the nonwoven fabric layers 11 and 12 is elastic filaments 13 of an SEBS resin or an SEPS resin and the nonwoven fabric layers 11 and 12 of PE sheath/PP core conjugate fibers or PE sheath/PET core conjugate fibers. In the case of using this combination, strong fusion bonding is ensured, and the conjugate fibers do not melt completely (the core remains non-fused) because of the high melting point of the core, thereby to provide the stretch sheet 10 with the highest possible strength.

The material constituting the nonstretch sheet 2 is described below.

Nonwoven fabrics by various processes are preferably used as the nonstretch sheet 2, including spun-bonded nonwoven, air-through nonwoven, and needle-punched nonwoven. Spun-bonded nonwoven fabric is particularly preferred. Spun-bonded nonwoven fabric preferably has the fibers oriented in the same direction as the direction in which the elastic filaments extend.

Fibers making up the first and second nonwoven fabric layers 11 and 12 and the nonstretch sheet 2 include polyethylene (PE) fibers, polypropylene (PP) fibers, polyester (PET or PBT) fibers, and polyamide fibers. The fibers composing the nonwoven fabric as the nonstretch sheet 2 may be staple fibers or continuous fibers and hydrophilic or water repellent. Sheath/core or side-by-side conjugate fibers, split fibers, and modified cross-section fibers are also useful. These fibers may be used either individually or in combination of two or more thereof. The nonwoven fabric may be continuous filament nonwoven or staple fiber nonwoven. A continuous filament nonwoven fabric is particularly preferred.

The stretchable composite sheet 1 according to the present embodiment is characterized by, for example, (1) the large number of regularly arranged ridges 3, (2) the presence of the fibers originated in the nonwoven fabric layer 12 inside the individual ridges 3 (see FIG. 2), (3) good hand and softness, and (4) good stretch properties. One or more of these characteristics taken advantage of the stretchable composite sheet 1 of the present embodiment is of wide utility.

For instance, the stretchable composite sheet 1 is useful as a component of an absorbent article. It is useful in other various applications, including surgical clothing and cleaning sheets. It is especially suited for use as a component of absorbent articles, like disposable diapers, incontinence pads, sanitary napkins, and panty liners. Examples of such a component include a fluid permeable sheet disposed on or above the skin facing side of an absorbent core (e.g., a topsheet, sublayer), a sheet defining the exterior surface of a disposable diaper, a sheet used to elasticize a waist portion, a below-waist portion, a leg portion, and the like of a disposable diaper, a sheet used to form stretchable wings of a winged sanitary napkin, and a sheet used to elasticize any other portion of an absorbent article.

In the cases where the stretchable composite sheet 1 is used as a component of an absorbent article, part or the whole of the process for the production of the stretchable composite sheet may be incorporated into the production line of an absorbent article manufacturing process.

Use of the stretchable composite sheet as a sheet defining the exterior surface of an absorbent article is exemplified by application to a pull-on type absorbent article (such as a pull-on diaper or a pull-on sanitary napkin) having an absorbent body and an exterior cover which is disposed on the garment-facing side of the absorbent body and to which the absorbent body is secured. The stretchable composite sheet is preferably used to form the exterior cover. In this case, the exterior cover may be totally formed of the stretchable composite sheet or, with the exterior cover being sectioned into a stomach portion adapted to be located on the stomach side of a wearer, a rear portion adapted to be located on the back side of a wearer, and a crotch portion, only the stomach portion and/or the rear portion of the exterior cover may be formed of the stretchable composite sheet. The absorbent body is usually composed of a liquid permeable topsheet, a liquid retentive absorbent core, and a hardly liquid permeable backsheet. In order to increase the constrictive force of a part of the exterior cover, such as the periphery of the waist opening or the periphery of the leg openings, an elastic member, like an elastic thread or tape, may be fixed to the part of the exterior cover. The pull-on type absorbent article of which the exterior cover is totally or partly formed of the stretchable composite sheet of the invention can be produced in a usual manner, except for using the stretchable composite sheet as a sheet material forming a part or the whole of the exterior cover. The processing steps for the production of the stretchable composite sheet may be incorporated into the production line of the absorbent article manufacturing process.

In the pull-on type absorbent article of which the exterior cover is totally or partly formed of the stretchable composite sheet of the invention, the stretchable composite sheet is used with its nonstretch sheet side facing either inside or outside of the exterior cover. When the nonstretch sheet side faces inside, because the ridges 3 are to be applied to the skin, there will be formed spaces between the skin and the valleys of the ridges 3. Air flows through the spaces to provide good breathability, and the skin-contacting side exerts good cushioning properties on the skin to provide good feel.

When the nonstretch sheet side faces outside, on the other hand, a diaper has an attractive appearance owing to the regularly arranged ridges on the exterior surface thereof.

Figure 8:
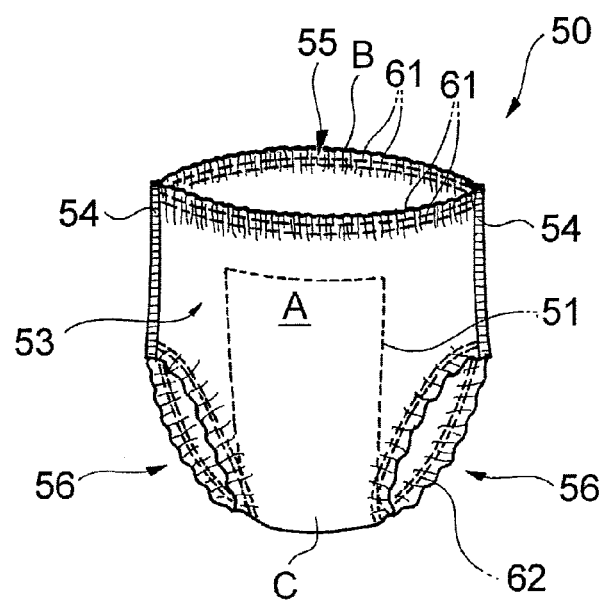
FIG. 8 is a perspective of a disposable pull-on diaper as an embodiment of the absorbent article according to the invention.
Figure 9:
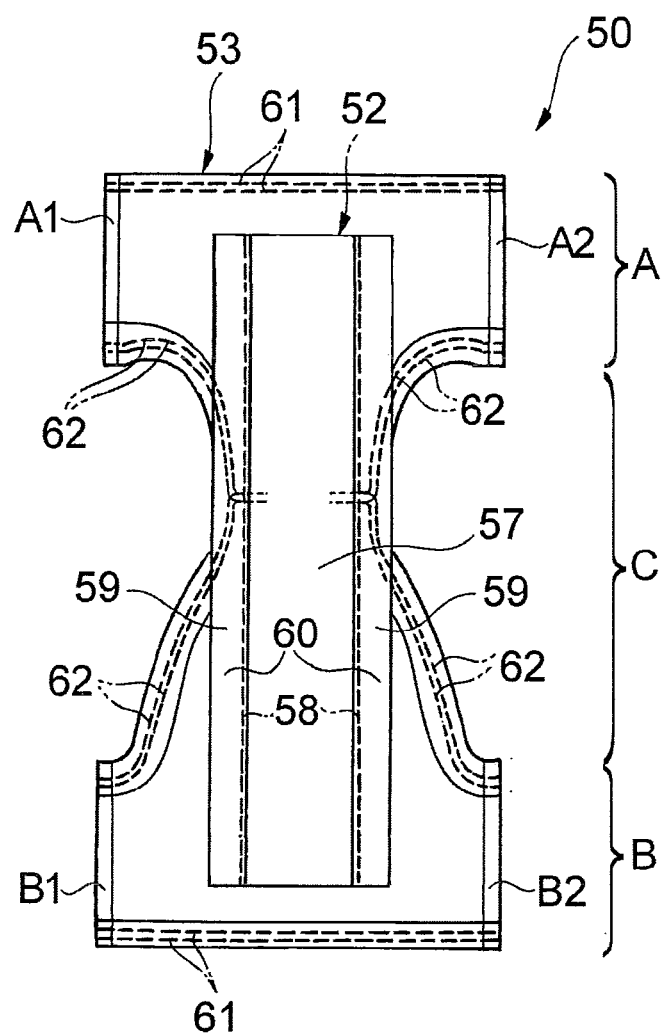
FIG. 9 is the diaper of FIG. 8 in its flat-out, stretched state.

FIGS. 8 and 9 illustrate an embodiment of a disposable pull-on diaper having an exterior cover formed of the stretchable composite sheet of the invention.

The disposable pull-on diaper 50 illustrated in FIGS. 8 and 9 has an absorbent body 52 including an absorbent core 51 and an exterior cover 53 which is disposed on the garment facing side of the absorbent body 52 and to which the absorbent body 52 is secured. As illustrated in FIGS. 8 and 9, the exterior cover has a stomach portion A, a rear portion B, and a crotch portion C. Both side edges A1 and A2 of the stomach portion A are joined to both side edges B1 and B2 of the rear portion B, respectively, to form a pair of side seals 54, a waist opening 55, and a pair of leg openings 56.

The absorbent body 52 includes a liquid permeable topsheet 57, a liquid impermeable or water repellent, leakproof sheet (not shown), and a liquid retentive absorbent core 51 interposed between the two sheets. The topsheet, leakproof sheet, and absorbent core can be of the same materials as conventionally used in this type of diapers. A leak preventive cuff-forming sheet 59 having an elastic member 58 along its free edge is provided on both lateral side edges of the absorbent body 52 to form a pair of side leak preventive cuffs 60.

The exterior cover 53 is totally formed of the stretchable composite sheet of the invention, specifically the above-described stretchable composite sheet 1. The stretchable composite sheet 1 is used with the direction in which the first and second zones 14 and 15 extend (i.e., direction X in FIGS. 1 and 3) coinciding with the longitudinal direction of the diaper (i.e., the longitudinal direction of the exterior cover 53 or the vertical direction of FIG. 9). The exterior cover 53 is formed of a single stretchable composite sheet 1 continuous from the stomach portion A to the rear portion B through crotch portion C. The stretchable composite sheet 1 is folded back inward along the periphery of the waist opening 55 and the leg openings 56, and waist elastic members 61 and leg elastic members 62 are fixed inside the respective folds. The elastic members 58, 61, and 62 may be of synthetic rubbers (e.g., styrene-butadiene rubber, butadiene rubber, isoprene rubber, and neoprene rubber), natural rubber, EVA, stretch polyolefins, polyurethane, etc. Forms of the elastic members 58, 61, and 62 include a thread with a rectangular, a square, a circular or a polygonal section (e.g., a rubber thread), tape (a rubber tape), or multifilamentous yarn.

The stretchable composite sheet 1 forming the exterior cover 53 of the diaper 50 is used with the nonstretch sheet 2 facing inside, i.e., to the wearer's skin. While worn, the diaper 50 has a large number of the ridges 3 on the inner side thereof to provide spaces between the skin and the valleys of the ridges 3. The diaper 50 therefore has good breathability, and its skin-contacting side with the ridges 3 feels good and gives no wet feel to the wearer.

Another embodiment of the disposable pull-on diaper of the invention has the exterior cover 53 formed of the stretchable composite sheet 1 with the side of the stretch sheet 10 facing inside. Having a large number of ridges 3 on the exterior surface of the diaper 50 in use, the diaper 50 has an attractive appearance.

In the case when the stretchable composite sheet 1, which has the nonstretch sheet 2 and the stretch sheet 10 united with an adhesive, is used to form the exterior cover 53, the coating weight of the adhesive applied between the nonstretch sheet 2 and the stretch sheet 10 is preferably 20 g/m$^2$ or less, more preferably 10 g/m$^2$ or less, even more preferably 5 g/m$^2$ or less, to provide the exterior cover 53 with good breathability. The coating weight of the adhesive as recited above is the amount (g) of the adhesive present between the stretch sheet 10 and the nonstretch sheet 2 per square meter of the stretchable composite sheet 1 in its natural, relaxed state.

The exterior cover 53 may have the amount of the adhesive applied varied from portion to portion. For instance, the amount of the adhesive in the stomach portion A and the rear portion B may be reduced to increase breathability, while that in the crotch portion C may be larger than in the stomach portion A and the rear portion B to ensure the fixing of the leg elastic members 62.

While the present invention has been described based on its preferred embodiments, the invention is not limited to the embodiments. For example, while the stretch sheet 10 used in the foregoing embodiments has a large number of elastic filaments 13 held between two nonwoven fabric layers 11 and 12, the stretch sheet used in the invention may be composed of a single layer of nonwoven fabric and a large number of elastic filaments bonded to the nonwoven fabric layer. The stretch sheet may have elastic film, elastic nonwoven fabric, or an elastic net in place of a large number of the elastic filaments 13 disposed between the nonwoven fabric layers 11 and 12. Whichever of such stretch sheets is used, it is preferred that the stretch sheet undergoes little contraction in width when stretched in the direction perpendicular to the direction in which the first and second zones 14 and 15 extend.

In the process for producing the stretchable composite sheet 1 illustrated in FIG. 4, the composite web 19 (a precursor of the stretch sheet 10) is stretched in the machine direction by the use of a pair of toothed rollers 20 ad 21 each having teeth and bottoms alternating in the circumferential direction. Alternatively, the composite web 19 may be stretched in the cross machine direction by using a pair of toothed rollers each having teeth and bottoms alternating in the axial direction. In the latter case, the resulting stretch sheet has the first regions and the second regions alternating in the transverse direction thereof. While in the stretchable composite sheet 1 of the foregoing embodiment the pitch P of the tops of the ridges 3 is about double the pitch of the first zones 14 or the second zones 15, the pitch P of the tops of the ridges 3 may be practically equal to the pitch of the first zones 14 or the second zones 15. The pitch P is adjusted by altering the pitch of the teeth of the toothed rollers.

The stretchable composite sheet of the invention may have either one of the stretch sheet and the nonstretch sheet extending from an edge of the other in addition to the overlapped area of the stretch sheet and the nonstretch sheet. The ridges may form not over the entire area of the overlap between the stretch sheet and the nonstretch sheet but only in part of the overlap. When the ridges are to form only in part of the overlap, the stretch sheet and the nonstretch sheet may be bonded on their facing sides over substantially the entire area of only a portion where the ridges are designed to form. Examples of a stretchable composite sheet designed to form ridges in only a portion thereof include a stretchable composite sheet designed to have no ridges in its peripheral portion, a stretchable composite sheet designed to have no ridges in a portion other than its peripheral portion, and a stretchable composite sheet in which portions having ridges and portions having no ridges alternate in the machine direction.

The size of the portion where the ridges form is preferably at least 1 cm, more preferably 2 cm or more, in both the first direction in which the first and second zones extend and the second direction perpendicular to the first direction in the natural, relaxed state of the stretchable composite sheet. The number of the ridges forming in that portion is preferably at least 3, more preferably 6 or more.

A plurality of the nonstretch sheets may be bonded to the stretch sheet in a spaced relation in the cross machine direction of the stretch sheet so that the ridges may form in a plurality of separate portions extending parallel to the machine direction. Conversely, a plurality of the stretch sheets may be bonded to the nonstretch sheet.

In the stretchable composite sheet of the invention, a different sheet laminated with the stretch sheet may be an extensible sheet having extensibility but not having stretchability or a second stretch sheet different from the above-mentioned stretch sheet. The same sheet as the stretch sheet 10 can be used as the second stretch sheet by changing the stretch ratio. In the case that the extensible sheet or the second stretch sheet is used as the different sheet, the preferable stretch ratio is less than 1.1, and its natural state (relaxed state before stretch) is more preferable. In the case where the extensible sheet or the second stretch sheet is used as the different sheet, the elongation at break is preferably 10% or more, more preferably 50% or more, and even more preferably 100% or more, when the different sheet is extended in perpendicular to the extending direction of the first and the second zones of the stretch sheet 10.

In addition, in the production process of the above-mentioned embodiment, a sheet that is joined and bonded to the stretch sheet 10 which is in its stretched state may be a stretch sheet or a extensible sheet in its natural state (relaxed state before stretch), in place of the nonstrech sheet 2. By joining and bonding the stretch or extensible sheet to the stretch sheet 10, a number of ridges are formed on the side of the sheet that is joined and bonded to the stretch sheet 10 which is in its stretch state.

EXAMPLES

The present invention will now be illustrated in greater detail with reference to Examples, but it should be understood that the invention is not deemed to be limited thereto.

Example 1

A stretchable composite sheet was prepared by bonding the stretch sheet and the nonstretch sheet described below by the following bonding method using an adhesive.

(a) Stretch Sheet

A composite web having two air through nonwoven fabric webs made of inelastic fibers and a large number of elastic filaments held therebetween was used as a stretch sheet precursor web. The elastic filaments in the stretch sheet precursor were arranged in a spaced parallel relation with each other.
Elastic filaments: made of a thermoplastic styrene elastomer; diameter: 120 to 130 μm
Weight of elastic filaments per unit area: 10 g/m$^2$
Inelastic fibers: PE sheath/PET core conjugate fibers; fineness: 3 dtex
Basis weight of each air through nonwoven fabric web made of inelastic fibers: 20 g/m$^2$ Basis weight of precursor web: 50 g/m²

The precursor web was fed in the direction in which the filaments lay and introduced into between a pair of toothed rollers with teeth and bottoms alternating in the circumferential direction, whereby the precursor web was stretched in the machine direction to provide a stretch sheet. Each toothed roller had a pitch of teeth of 2 mm, a tooth height of 3.5 mm, a tooth thickness of 0.5 mm.

The resulting stretch sheet had first zones of 1.4 to 1.6 mm in width and second zones of 0.4 to 0.5 mm in width alternating with each other in the machine direction. When the stretch sheet was stretched 2.0 times in the direction perpendicular to the direction in which the first and the second zones extended, i.e., in the machine direction, the width retention of the stretch sheet was 93% to 95% with respect to the width before the stretch.

(b) Nonstretch Sheet

Spun-bonded nonwoven fabric made of PE sheath/PET core conjugate fibers; basis weight: 18 g/m²

(c) Method of Bonding

A hot melt adhesive (styrene-based, styrene-butadiene-styrene block copolymer rubber) was applied to substantially the entire area of the nonstretch sheet at 150° C. with a coater gun to give a coating weight of 1.0 g/m². The stretch sheet was stretched 1.7 times the original length and joined in the stretched state to the adhesive-coated side of the nonstretch sheet to make a stretchable composite sheet.

The resulting stretchable composite sheet had a large number of ridges extending in the direction perpendicular to the machine direction (the same as the direction in which the first and second zones of the stretch sheet extended) on the nonstretch sheet side.

Example 2

The same stretch sheet, nonstretch sheet, and hot melt adhesive as used in Example 1 were used. The hot melt adhesive was applied to the nonstretch sheet at the same coating weight by the same coating method as in Example 1. The stretch sheet was stretched 2.0 times the original length and bonded in the stretched state to the adhesive-coated side of the nonstretch sheet to give a stretchable composite sheet.

The resulting stretchable composite sheet had a large number of ridges extending in the direction perpendicular to the machine direction (the same as the direction in which the first and second zones of the stretch sheet extended) on the nonstretch sheet side.

Comparative Example 1

The same stretch sheet, nonstretch sheet, and adhesive as used in Example 1 were used. The hot melt adhesive was applied to the nonstretch sheet in a dot pattern, the dots being 2 mm diameter circles spaced apart a distance of 5 mm in the transverse direction and 8 mm in the longitudinal direction. The area ratio of the dots was 4.2%. The coating weight was 1 g per square meter of the dots. The stretch sheet was stretched 1.7 times the original length and bonded in the stretched state to the adhesive-coated side of the nonstretch sheet to give a stretchable composite sheet.

The resulting stretchable composite sheet had projections between the dots on the nonstretch sheet side but no ridges extending in one direction.

Evaluation:

(1) Regularity and Appearance of Surface Texture

The surface of the stretchable composite sheets obtained in Examples 1 and 2 and Comparative Example 1 was observed with a microscope to measure the pitch and the height of ten ridges adjacent to each other in the machine direction. The results obtained are shown in Table 1 below. The pitch and the height correspond to P and T designated in FIG. 2. In Comparative Example 1, projections adjacent to each other in the machine direction were taken for the measurement of pitch and height, the projections being called "ridges" in Table 1 for the sake of convenience.

TABLE 1

|  | Example 1 | Example 2 | Compara. Example 1 |
|---|---|---|---|
| Pitch P of Ridges (mm) | 1.8-2.0 | 1.8-2.0 | 1.6-2.1 |
| Height T of Ridges (mm) | 1.6-1.8 | 1.8-2.0 | 1.3-1.9 |

As shown in Table 1, the stretchable composite sheets of Examples 1 and 2 form regular ridges with less variations in pitch and height than the stretchable composite sheet of Comparative Example 1.

The stretchable composite sheet of Comparative Example 1 form projections which are not ridges extending in one direction. The projections show variations in pitch and height and cannot be said to be regular. The appearance of the stretchable composite sheet was unattractive.

(2) Breathability

The stretchable composite sheets obtained in Examples 1 and 2 and Comparative Example 1 were tested for breathability as follows.

Breathability was evaluated in terms of air permeability as measured in accordance with the following test method.

A specimen measuring 50 mm by 100 mm was cut out of each stretchable composite sheet. The specimen was set on an air permeability tester KES-F8-AP1 from Kato Tech Co., Ltd. to cover the vent in a state stretched 1.5 times in its longitudinal direction, and air permeating resistance R (unit: kPa·sec/m) was measured. The permeating resistance R was converted to air permeability Q (unit: cc/cm²·sec) according to formula: Q=12.5/R.

The test was carried out in quintuplicate (n=5) for each stretchable composite sheet to obtain an average. The results obtained are shown in Table 2. A higher air permeability value indicates higher breathability of the sheet.

TABLE 2

|  | Example 1 | Example 2 | Comp. Example 1 |
|---|---|---|---|
| Air Permeability (cc/cm² · sec) | 503 | 495 | 483 |

The results in Table 2 prove that the stretchable composite sheets of Examples 1 and 2 having a hot melt adhesive applied to substantially the entire area of the sheets and the stretchable composite sheet of Comparative Example 1 having a hot melt adhesive applied discretely are equal in breathability.

(3) Softness

The stretchable composite sheets of Examples 1 and 2 and Comparative Example 1 were evaluated for appearance, softness, and feel to the touch by five panelists who are above twenty years and less than fifty years old. The appearance was evaluated visually, and softness and feel were evaluated by touch. The samples of Examples 1 and 2 were scored 2 (better than Comparative Example 1), 1 (equal to Comparative Example 1), or 0 (worse than Comparative Example 1).

Table 3 below shows the averages of the scores by the five panelists. An average score exceeding 1 means superiority to Comparative Example 1, and an average score less than 1 indicates inferiority to Comparative Example 1.

TABLE 3

|  | Example 1 vs. Comp. Example 1 | Example 2 vs. Comp. Example 1 |
|---|---|---|
| Appearance | 1.8 | 1.2 |
| Softness | 1.4 | 1.6 |
| Feel | 1.6 | 1.6 |

Examples 1 and 2 were proved superior to Comparative Example 1 in all of appearance, feel, and softness. The panelists selected one sample they rated the best by comprehensive evaluation. Four selected the sample of Example 1, and one selected the sample of Comparative Example 1.

INDUSTRIAL APPLICABILITY

The stretchable composite sheet of the present invention has a large number of ridges in a neat and orderly arrangement and is easily produced by the process according to the invention. The absorbent article of the present invention has a large number of ridges in a neat and orderly arrangement and is easily produced by the process of the invention.

The invention claimed is:

1. A stretchable composite sheet comprising a stretch sheet and a nonstretch sheet laminated with the stretch sheet and having a first direction and a second direction perpendicular to the first direction,
   the stretch sheet having a first zone with elastic stretchability and a second zone with less elastic stretchability than that of the first zone, the first and the second zones extending in the first direction and alternate in the second direction,
   the stretch sheet and the nonstretch sheet being bonded to each other on their facing sides,
   the stretchable composite sheet as a whole having stretchability in at least the second direction, and
   the stretchable composite sheet having, in a natural, relaxed state, a large number of ridges extending in the first direction on the nonstretch sheet side in a portion where the stretch sheet and the nonstretch sheet are bonded to each other over substantially the entire area;
   wherein a pitch of the ridges is 0.5 to 5 mm and a height of the ridges is 0.5 to 5 mm;
   wherein the stretch sheet comprises an extensible nonwoven fabric and a large number of elastic filaments bonded to the nonwoven fabric in their substantially nonstretched state over the whole length thereof, the elastic filaments being arranged to extend in the same direction without intersecting with each other, and the stretch sheet having stretchability in the direction in which the elastic filaments extend;
   wherein the direction in which the elastic filaments extend is perpendicular to the first direction;
   wherein the stretchable composite sheet has second ridges that protrude on the opposite side of the ridges and on the side that the nonstretch sheet is not bonded; and
   wherein the second ridges extend in the same direction as the ridges, are formed between the ridges that the second ridges are adjacent to, and are shorter than the height of the ridges.

2. The stretchable composite sheet according to claim 1, wherein the stretch sheet has a width retention of 70% to 100% with respect to the width before the stretch when stretched 2.0 times in the second direction.

3. The stretchable composite sheet according to claim 1, wherein the stretch sheet is obtained by stretching a precursor sheet of the stretch sheet between a pair of intermeshing toothed surfaces each having alternate ridges and grooves to form the first and the second zones in the precursor sheet.

4. An absorbent article comprising the stretchable composite sheet according to claim 1.

5. The absorbent article according to claim 4, which is a pull-on type absorbent article comprising an absorbent body and an exterior cover which is disposed on the garment-facing side of the absorbent body and to which the absorbent body is secured,
   wherein the exterior cover is formed totally or partly of the stretchable composite sheet.

6. The stretchable composite sheet according to claim 1, wherein the elastic filaments are in a substantially nonstretched state at the time of bonding to the nonwoven fabric.

7. The stretchable composite sheet according to claim 1, wherein the stretch sheet is obtained by stretching a precursor sheet of the stretch sheet; and
   wherein the precursor sheet comprises webs of the nonwoven fabric that are inextensible.

8. The stretchable composite sheet according to claim 1, wherein the elastic filaments are fixed to the nonwoven fabric in their substantially nonstretched state.

9. The stretchable composite sheet according to claim 1, wherein the elastic filaments are formed by drawing a filamentous elastic resin in a molten or softened state;
   wherein the molten or softened elastic filaments are sandwiched between a first layer of the nonwoven fabric and a second layer of the nonwoven fabric that are unrolled and fed at equal speeds; and
   wherein the sandwiched elastic filaments are taken off at a predetermined speed that is equal to the feed speed of the first and second layers of the nonwoven fabric.

10. The stretchable composite sheet according to claim 1, wherein the stretch sheet is obtained by stretching a precursor sheet of the stretch sheet in the direction in which the elastic filaments extend while being passed between a pair of intermeshing toothed surfaces each having alternate ridges and grooves.

11. The stretchable composite sheet according to claim 10, wherein regions of the precursor sheet are thinner because the regions are pressed radially.

12. A process for producing a stretchable composite sheet comprising a stretch sheet and a nonstretch sheet laminated with the stretch sheet, having a first direction and a second direction perpendicular to the first direction, and having in its natural, relaxed state a large number of ridges all over the area or in at least part of the nonstretch sheet side thereof, the stretch sheet having a first zone with elastic stretchability and a second zone with less elastic stretchability than that of the first zone, and the first and second zones extending in the first direction and alternate in the second direction,
   the process comprising bonding the stretch sheet and the nonstretch sheet to each other via an adhesive while the stretch sheet is in its stretched state such that the two sheets are bonded on their facing sides over substantially the entire area of a portion where the large number of ridges are to form;
   wherein a pitch of the ridges is 0.5 to 5 mm and a height of the ridges is 0.5 to 5 mm;
   wherein the stretch sheet is obtained by stretching a precursor sheet of the stretch sheet between a pair of intermeshing toothed surfaces each having alternate ridges and grooves to form the first and the second zones on the precursor sheet;

wherein the stretch sheet is bonded to the nonstretch sheet while the stretch sheet is in a stretched state;

wherein the stretch sheet comprises an extensible nonwoven fabric and a large number of elastic filaments bonded to the nonwoven fabric in their substantially nonstretched state over the whole length thereof, the elastic filaments being arranged to extend in the same direction without intersecting with each other, and the stretch sheet having stretchability in the direction in which the elastic filaments extend;

wherein the elastic filaments are formed by drawing a filamentous elastic resin in a molten or softened state;

wherein the precursor sheet comprises webs of the nonwoven fabric that are inextensible; and wherein a large number of elastic filaments extruded from a spinning nozzle are fusion bonded to the nonwoven fabric before solidifying while being drawn at a predetermined speed and oriented in one direction without intersecting with each other in order to form the stretch sheet.

13. The process for producing a stretchable composite sheet according to claim 12, wherein the stretch sheet is bonded to the nonstretch sheet while the stretch sheet is in a state stretched 1.1 to 4.0 times in one of the machine direction and the cross machine direction.

14. The process for producing a stretchable composite sheet according to claim 12, wherein the adhesive is applied to a coating weight of 0.5 to 20 g/m$^2$.

* * * * *